USOO5654419A

United States Patent [19]
Mathies et al.

[11] Patent Number: 5,654,419
[45] Date of Patent: Aug. 5, 1997

[54] FLUORESCENT LABELS AND THEIR USE IN SEPARATIONS

[75] Inventors: Richard A. Mathies, El Cerrito; Alexander Glazer, Orinda; Jingyue Ju, Berkeley, all of Calif.

[73] Assignee: The Regents of the University of California, Oakland, Calif.

[21] Appl. No.: 189,924

[22] Filed: Feb. 1, 1994

[51] Int. Cl.[6] .............................. C07H 21/00; C12Q 1/68
[52] U.S. Cl. ...................... 536/25.4; 435/6; 435/810; 436/501; 436/63; 536/22.1; 536/23.1; 935/77; 935/78
[58] Field of Search ........................... 435/5, 6, 7.1, 810; 436/501, 63; 536/22.1, 23.1, 25.4; 935/77, 78

[56] References Cited

U.S. PATENT DOCUMENTS

| | | |
|---|---|---|
| 4,996,143 | 2/1991 | Heller et al. ................................. 435/6 |
| 5,188,934 | 2/1993 | Menchen et al. ........................... 435/6 |
| 5,326,692 | 7/1994 | Brinkley et al. ............................ 435/6 |

OTHER PUBLICATIONS

Geysen et al. (1988) Journal of Molecular Recognition, vol. 1, No. 1, pp. 32–41.

Ansorge et al., "Automated DNA Sequencing: Ultrasensitive Detection of Fluorescent Bands During Electrophoresis", *Nucleic Acids Research* 15(11):4593–4602 (1987).

Cardullo et al., "Detection of Nucleic Acid Hybridization by Nonradiative Fluorescence Resonance Energy Transfer", *Proc. Natl. Acad. Sci. USA* 85:8790–8794 (1988).

Clegg et al., "Fluorescence Resonance Energy Transfer Analysis of the Structure of the Four-Way DNA Junction", *Biochemistry* 31(20):4846–4856 (1992).

Huang et al., "DNA Sequencing Using Capillary Array Electrophoresis", *Anal. Chem.* 64(18):2149–2154 (1992).

Maliwal et al., "End–to–end Diffusion Coefficients and Distance Distributions from Fluorescence Energy Transfer Measurements: Enhanced Resolution by Using Multiple Acceptors with Different Förster Distances", *Biophysical Chemistry* 46:273–281 (1993).

Mathies and Huang "Capillary Array Electrophoresis: An Approach to High–speed, High–throughput DNA Sequencing", *Nature* 359:167–169 (1992).

Middendorf et al., "Continuous, On–line DNA Sequencing Using a Versatile Infrared Laser Scanner/Electrophoresis Apparatus", *Electrophoresis* 13:487–494 (1992).

Montenay–Garestier et al., "Design of Bifunctional Nucleic Acid Ligands", *Molecular Basis of Specifity in Nucleic Acid–Drug Interactions*, pp. 275–290 (1990), B. Pullman and J. Jortner (eds).

Prober et al., "A System for Rapid DNA Sequencing with Fluorescent Chain–Terminating Dideoxynucleotides", *Science* 238:336–341 (1987).

Ruth et al., "Linker Arm Nucleotide Analogs Useful in Oligonucleotide Synthesis", *DNA* 4:93 (1985) (Abstract).

Sanger et al., "DNA Sequencing with Chain–terminating Inhibitors", *Proc. Natl. Acad. Sci. USA* 74(12):5463–5467 (1977).

(List continued on next page.)

*Primary Examiner*—W. Gary Jones
*Assistant Examiner*—Ardin H. Marschel
*Attorney, Agent, or Firm*—Bertram I. Rowland

[57] ABSTRACT

Compositions are provided comprising sets of fluorescent labels carrying pairs of donor and acceptor dye molecules, designed for efficient excitation of the donors at a single wavelength and emission from the acceptor in each of the pairs at different wavelengths. The different molecules having different donor-acceptor pairs can be modified to have substantially the same mobility under separation conditions, by varying the distance between the donor and acceptor in a given pair. Particularly, the fluorescent compositions find use as labels in sequencing nucleic acids.

11 Claims, 7 Drawing Sheets
(7 of 7 Drawing(s) in Color)

OTHER PUBLICATIONS

Smith et al., "The Synthesis of Oligonucleotides Containing an Aliphatic Amino Group at the 5' Terminus: Synthesis of Fluorescent DNA Primers for Use in DNA Sequence Analysis", *Nucleic Acids Research* 13(7):2399–2412 (1985).

Smith et al., "Fluorescence Detection in Automated DNA Sequence Analysis", *Nature* 321:674–679 (1986).

Stryer, "Fluorescence Energy Transfer as a Spectroscopic Ruler", *Ann. Rev. Biochemistry* 47:819–846 (1978).

Stryer and Haugland, "Energy Transfer: A Spectroscopic Ruler", *Proc. Natl. Acad. Sci. USA* 58:719–726 (1967).

Theisen et al., "Fluorescent Dye Phosphoramidite Labeling of Oligonucleotides", *Tetrahedron Letters* 33(35):5033–5036 (1992).

FLUORESCENT LABELS AND THEIR USE IN SEPARATIONS

TECHNICAL FIELD

The field of this invention is fluorescent tags and their use.

BACKGROUND

There is an increasing demand to be able to identify and quantify components of mixtures. The greater the complexity of the mixture, the greater the interest in being able to simultaneously detect a plurality of the components present. As illustrative of this situation is DNA sequencing, where it is desirable to efficiently excite from one to four fluorescently tagged components with a laser source at a single wavelength, while providing for fluorescent signal emission at a plurality of distinctive wavelengths. In this situation, the different labels should not adversely affect the electrophoretic mobility of the sequences to which they are attached.

Currently, there are four methods used for automated DNA sequencing: (1) the DNA fragments are labeled with one fluorophore and then the fragments run in adjacent sequencing lanes (Ansorge et al., *Nucleic Acids Res.* 15, 4593–4602 (1987); (2) the DNA fragments are labeled with four different fluorophores and all the fragments are electrophoretically separated and detected in a single lane (Smith et al., *Nature* 321, 674–679 (1986); (3) each of the dideoxynucleosides in the termination reaction is labeled with a different fluorophore and the four sets of fragments are run in the same lane (Prober et al., *Science* 238,336–341 (1987); or (4) the sets of DNA fragments are labeled with two different fluorophores and the DNA sequences coded with the dye ratios (Huang et al., *Anal. Chem.* 64, 2149–2154 (1992).

All of these techniques have significant deficiencies. Method 1 has the potential problems of lane-to-lane variations in mobility, as well as a low throughput. Methods 2 and 3 require that the four dyes be well excited by one laser source and that they have distinctly different emission spectra. In practice, it is very difficult to find two or more dyes that can be efficiently excited with a single laser and that emit well separated fluorescent signals.

As one selects dyes with distinctive red-shifted emission spectra, their absorption maxima will also move to the red and all the dyes can no longer be efficiently excited by the same laser source. Also, as more different dyes are selected, it becomes more difficult to select all the dyes such that they cause the same mobility shift of the labeled molecules.

It is therefore of substantial interest that improved methods be provided which allow for multiplexing of samples, so that a plurality of components can be determined in the same system and in a single run. It is also desirable for each label to have strong absorption at a common wavelength, to have a high quantum yield for fluorescence, to have a large Stokes shift of the emission, that the various emissions be distinctive, and that the labels introduce the same mobility shift. It is difficult to accomplish these conflicting goals by simply labeling the molecules with a single dye.

SUMMARY OF THE INVENTION

The subject invention provides compositions and methods for analyzing a mixture using a plurality of fluorescent labels. To generate the labels, pairs or families of fluorophores are bound to a backbone, particularly a nucleic acid backbone, where one of the members of the families is excited at about the same wavelength. By exploiting the phenomenon of energy transfer, the other members of each of the families emit at detectably different wavelengths. The range of distances between donor and acceptor chromophores is chosen to ensure efficient energy transfer. Furthermore, labels used conjointly are selected to have approximately the same mobility in a separation system. This is achieved by changing the mobility of the labeled entity by varying the distance between the two or more members of the family of fluorophores and choosing labels with the same mobility. The subject invention finds particular application in sequencing, where the fluorophores may be attached to universal or other primers and different fluorophore combinations used for the different dideoxynucleosides. Kits of combinations of labels are also provided.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DESCRIPTION OF SPECIFIC EMBODIMENTS

Novel fluorescent labels, combinations of fluorescent labels, and their use in separation systems involving the separation of a plurality of components are provided. Particularly, the fluorescent labels comprise pairs of fluorophores, which with one exception where the fluorophores are the same, involve different fluorophores having overlapping spectra, where the donor emission overlaps the acceptor absorption, so that there is energy transfer from the excited fluorophore to the other member of the pair. It is not essential that the excited fluorophore actually fluoresce, it being sufficient that the excited fluorophore be able to efficiently absorb the excitation energy and efficiently transfer it to the emitting fluorophore.

The donor fluorophores in the different families of fluorophores may be the same or different, but will be able to be excited efficiently by a single light source of narrow bandwidth, particularly a laser source. The donor fluorophores will have significant absorption, usually at least about 10%, preferably at least about 20% of the absorption maxima within 20 nm of each other, usually within 10 nm, more usually within 5 nm, of each other. The emitting or accepting fluorophores will be selected to be able to receive the energy from donor fluorophores and emit light, which will be distinctive and detectably different. Therefore, one will be able to distinguish between the components of the mixture to which the different labels have been bound. Usually the labels will emit at emission maxima separated by at least 10 nm, preferably at least 15 nm, and more preferably at least 20 nm.

Usually the donor fluorophores will absorb in the range of about 350–800 nm, more usually in the range of about 350–600 nm or 500–750 nm, while the acceptor fluorophores will emit light in the range of about 450–1000 nm, usually in the range of about 450–800 nm. As will be discussed subsequently, one may have more than a pair of absorbing molecules, so that one may have 3 or more molecules, where energy is transferred from one molecule to the next at higher wavelengths, to greatly increase the difference in wavelength between absorption and observed emission.

The two fluorophores will be joined by a backbone or chain, usually a polymeric chain, where the distance between the two fluorophores may be varied. The physics behind the design of the labels is that the transfer of the optical excitation from the donor to the acceptor depends on $1/R^6$, where R is the distance between the two fluorophores. Thus, the distance must be chosen to provide efficient energy transfer from the donor to the acceptor through the well-known Foerster mechanism. Thus, the distance between the two fluorophores as determined by the number of atoms in the chain separating the two fluorophores can be varied in accordance with the nature of the chain. Various chains or backbones may be employed, such as nucleic acids, both DNA and RNA, modified nucleic acids, e.g. where oxygens may be substituted by sulfur, carbon, or nitrogen, phosphates substituted by sulfate or carboxylate, etc., polypeptides, polysaccharides, various groups which may be added stepwise, such as di-functional groups, e.g. haloamines, or the like. The fluorophores may be substituted as appropriate by appropriate functionalization of the various building blocks, where the fluorophore may be present on the building block during the formation of the label, or may be added subsequently, as appropriate. Various conventional chemistries may be employed to ensure that the appropriate spacing between the two fluorophores is obtained.

The molecular weights of the labels (fluorophores plus the backbone to which they are linked) will generally be at least about 250 Dal and not more than about 5,000 Dal, usually not more than about 2,000 Dal. The molecular weight of the fluorophore will generally be in the range of about 250 to 1,000 Dal, where the molecular weights of the acceptor-donor pairs on different labels to be used together will usually not differ by more than about 20%. The fluorophores may be bound internal to the chain, at the termini, or one at one terminus and another at an internal site. The fluorophores may be selected so as to be from a similar chemical family, such as cyanine dyes, xanthenes or the like. Thus, one could have the donors from the same chemical family, each donor-acceptor pair from the same chemical family or each acceptor from the same family.

The subject labels find particular application in various separation techniques, such as electrophoresis, chromatography, or the like, where one wishes to have optimized spectroscopic properties, high sensitivity and comparable influence of the labels on the migratory aptitude of the components being analyzed. Of particular interest is electrophoresis, such as gel, capillary, etc. Among chromatographic techniques are HPLC, affinity chromatography, thin layer chromatography, paper chromatography, and the like.

It is found that the spacing between the two fluorophores will affect the mobility of the label. Therefore, one can use different dye pairs and by varying the distance between the different dye pairs, within a range which still permits good energy transfer, provide for substantially constant mobility for the labels. The mobility is not related to the specific spacing, so that one will empirically determine the effect of the spacing on the mobility of a particular label. However, because of the flexibility in the spacing of the fluorophores in the labels, by synthesizing a few different labels with different spacings and different dye pairs, one can now provide for a family of fluorescent labels, which share a common excitation, that have strong and distinctive emission and a substantially common mobility. Usually, the mobility will differ by not more than about 20% of each other, preferably not more than about 10% of each other, and more preferably within about 5% of each other, when used in a particular separation. The mobility may usually be determined by carrying out the separation of the labels by themselves or the labels bound to a common molecule which is relevant to the particular separation, e.g. a nucleic acid molecule of the appropriate size, where one is interested in sequencing.

A wide variety of fluorescent dyes may find application. These dyes will fall into various classes, where combinations of dyes may be used within the same class or between different classes. Included among the classes are dyes, such as the xanthene dyes, e.g. fluoresceins and rhodamines, coumarins, e.g. umbelliferone, benzimide dyes, e.g. Hoechst 33258, phenanthridine dyes, e.g. Texas Red, and ethidium dyes, acridine dyes, cyanine dyes, such as thiazole orange, thiazole blue, Cy 5, and Cyfr, carbazole dyes, phenoxazine dyes, porphyrin dyes, quinoline dyes, or the like. Thus, the dyes may absorb in the ultraviolet, visible or infra-red ranges. For the most part, the fluorescent molecules will have a molecular weight of less than about 2 kDal, generally less than about 1.5 kDal.

The energy donor should have strong molar absorbance coefficient at the desired excitation wavelength, desirably greater than about $10^4$, preferably greater than about $10^5$ $cm^{-1}M^{-1}$. The excitation maximum of the donor and the emission maximum of the acceptor (fluorescer) will be separated by at least 15 nm or greater. The spectral overlap integral between the emission spectrum of the donor chromophore and the absorption spectrum of the acceptor chromophore and the distance between the chromophores will be such that the efficiency of energy transfer from donor to acceptor will range from 20% to 100%.

Separation of the donor and acceptor based on number of atoms in the chain will vary depending on the nature of the backbone, whether rigid or flexible, involving ring structures or non-cyclic structures or the like. Generally the number of atoms in the chain (the atoms in the ring structures will be counted as the lowest number of atoms around one side of the ring for inclusion in the chain) will be below about 200, usually below about 150 atoms, preferably below about 100, where the nature of the backbone will influence the efficiency of energy transfer between donor and acceptor.

While for the most part, pairs of fluorophores will be used, there can be situations where up to four different, usually not more than three different, fluorophores bound to the same backbone may find use. By using more fluorophores, one may greatly extend the Stokes shift, so that one may excite in the visible wavelength range and emit in the infra-red wavelength range, usually below about 1000 nm, more usually below about 900 nm. Detecting light in the infra-red wavelength range has many advantages, since it will not be subject to interference from Raman and Rayleigh light resulting from the excitation light. In order to maintain the mobility constant, one may use the same number of fluorophores on the labels, having a multiplicity of the same fluorophore to match the number of fluorophores on labels having different fluorophores for the large Stokes shift.

The subject invention finds particular application with nucleic acid chains, where the nucleic acid chains find use as primers in sequencing, the polymerase chain reaction, particularly for sizing, or other system where primers are employed for nucleic acid extension and one wishes to distinguish between various components of the mixture as related to the particular labels. For example, in sequencing, universal primers may be employed, where a different pair of fluorophores are used for each of the different dideoxynucleosides used for the extension during sequencing.

A large number of nucleosides are available, which are functionalized, and may be used in the synthesis of a polynucleotide. By synthesizing the subject nucleic acid labels, one can define the specific sites at which the fluorophores are present. Commercially available synthesizers may be employed in accordance with conventional ways, so that any sequence can be achieved, with the pair of fluorophores having the appropriate spacing.

Where different primers have been used in PCR, each of the primers may be labeled in accordance with the subject invention, so that one can readily detect the presence of the target sequence complementary to each of the different primers. Other applications which may find use include identifying isozymes, using specific antibodies, identifying lectins using different polysaccharides, and the like. As already indicated, the subject labels find particular use in sequencing. For example, universal primers may be prepared, where the primer may be any one of the universal primers, having been modified by bonding of the two fluorophores to the primer. Thus, various commercial primers are available, such as primers from pUC/M13, λgt10, λgt11, and the like. See, Sambrook et al., Molecular Cloning: A Laboratory Manual, 2nd ed., CSHL, 1989, Section 13. DNA sequences are cloned in an appropriate vector having a primer sequence joined to the sequence to be sequenced. Different 2', 3' ddNTPs are employed, so that termination occurs at different sites, depending upon the particular ddNTP which is present in the chain extension. By employing the subject primers, each ddNTP will be associated with a particular label. After extension with the Klenow fragment, the resulting fragments may then be separated in a single lane by electrophoresis or in a single capillary by electrophoresis, where one can detect the terminating nucleotide by virtue of the fluorescence of the label. One may also use the subject labels with immune complexes, where the ligands or receptors, e.g. antibodies, may be labeled to detect the different complexes or members of the complexes. Where the ligands may have the same migratory aptitude in the method separation, to determine the presence of one or more of such ligands, the different antibodies could be labeled with the different labels fluorescing at different wavelengths, so as to be detectable, even where there is overlap of the compositions in the separation.

Kits are provided having combinations of labels, usually at least 2. Each of the labels will have the acceptor-donor pair, usually with comparable backbones, where the labels will be separated along the backbone to give comparable mobility in the separation method to be used. Each of the labels in a group to be used together will absorb at about the same wavelength and emit at different wavelengths. Each of the labels in the group will have about the same effect on mobility in the separation method, as a result of the variation in placement of the different fluorophores along the backbone.

The kits will generally have up to about 6, usually about up to about 4 different labels which are matching, but may have 2 or more sets of matching labels, having 2–6 different labels.

Of particular interest are labels comprising a nucleic acid backbone, where the labels will generally have at least about 10 nucleotides and not more than about 50 nucleotides, usually not more than about 30 nucleotides. The labels may be present on the nucleotides which hybridize to the complementary sequence or may be separated from those nucleotides. The fluorophores will usually be joined to the nucleotide by a convenient linking arm of from about 2 to 20, usually 4 to 16 atoms in the chain. The chain may have a plurality of functionalities, particularly non-oxo-carbonyl, more particularly ester and amide, amino, oxy, and the like. The chain may be aliphatic, alicyclic, aromatic, heterocyclic, or combinations thereof, usually comprising carbon, nitrogen, oxygen, sulfur, or the like in the chain.

The entire nucleic acid sequence may be complementary to the 5' primer sequence or may be complementary only to the 3' portion of the sequence. Usually, there will be at least about 4 nucleotides, more usually at least about 5 nucleotides which are complementary to the sequence to be copied. The primers are combined with the sequence to be copied in the appropriate plasmid having the primer sequence at the 3' end of the strand to be copied and dNTPs added with a small amount of the appropriate ddntp. After extension, the DNA may be isolated and transferred to a gel or capillary for separation.

The kits which are employed will have at least two of the subject labels, which will be matched by having substantially the same absorption for the donor molecule, distinct emission spectra and substantially the same mobility. Generally for single stranded nucleic acids, the separation will be from about 1–15, more usually 1–12, preferably about 2–10 nucleosides between fluorophores.

The following examples are offered by way of illustration and not by way of limitation.

EXPERIMENTAL

Design and Synthesis of Energy Transfer Fluorescent Dye Tagged Oligonucleotide Labels for Genetic Analysis.

Deoxyoligonucleotides (12-base long) with the sequence 5=-GTTTTCCCAGTC-3', selected from the M13 universal primer, were synthesized with donor-acceptor fluorophore pairs separated by different distances. Specifically, the 12-mer contains a modified base introduced by the use of 5 'dimethoxytrityl-5-[N-(trifluoroacetylaminohexy)-3-acrylimido]-2'-deoxyUridine, 3'-[(2-cyanoethyl)-(N,N- diisopropyl)]-phosphoramidite (Amino-Modifier C6 dT) (Structure 1), which has a primary amine linker arm at the C-5 position.

Structure 1.
Amino-Modifier C6 dT

Figure 2:
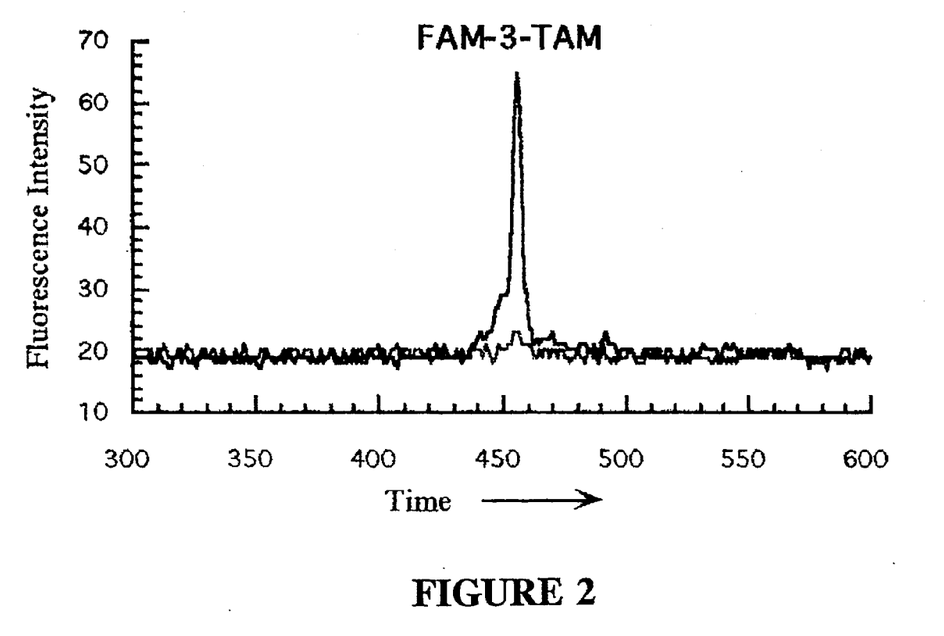
FIG. 2 is a CE electropherogram of FAM-3-TAM. The sample was analyzed by typical capillary electrophoresis DNA sequencing conditions with 488 nm excitation. The green trace is the fluorescence signal detected in the green channel (525 nm), and the red trace is the fluorescence signal detected in the red channel (590 nm). Both channels are detected simultaneously.
Figure 3:
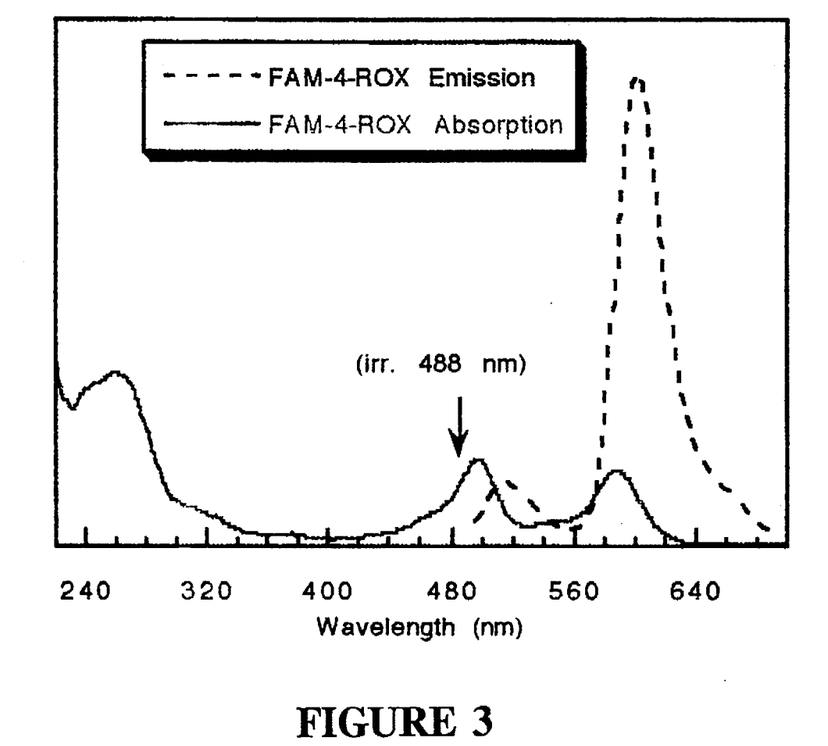
FIG. 3 is a graph of the absorption and emission spectra of FAM-4-ROX in 1xTBE.
Figure 4:
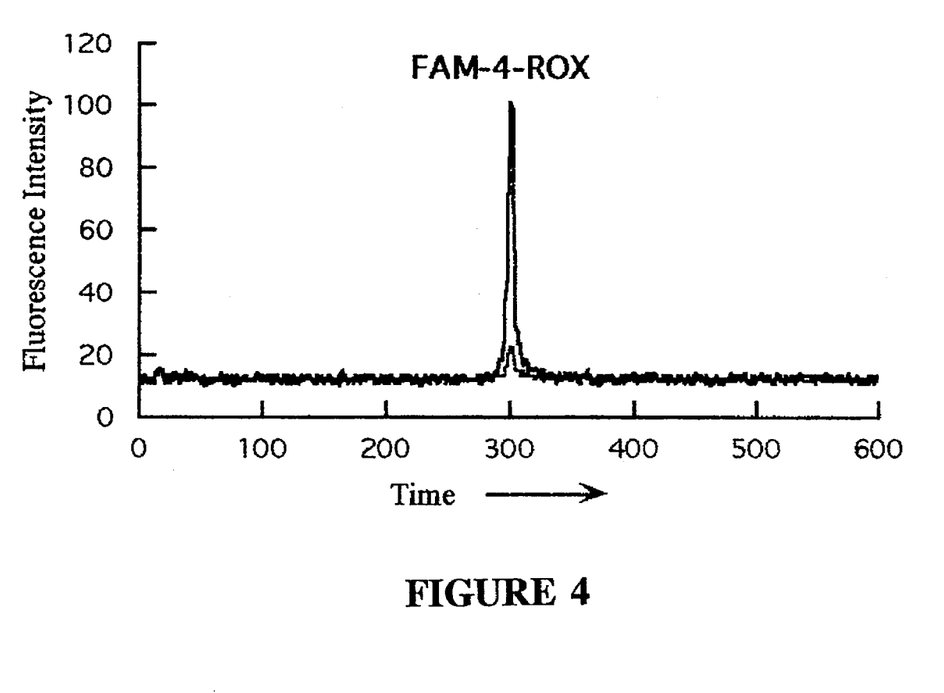
FIG. 4 is a CE electropherogram of FAM-4-ROX. The sample was analyzed by typical capillary electrophoresis DNA sequencing conditions with 488 nm excitation. The green trace is the fluorescence signal detected in the green channel (525 nm), and the red trace is the fluorescence signal detected in the red channel (590 nm). Both channels are detected simultaneously.
Figure 5:
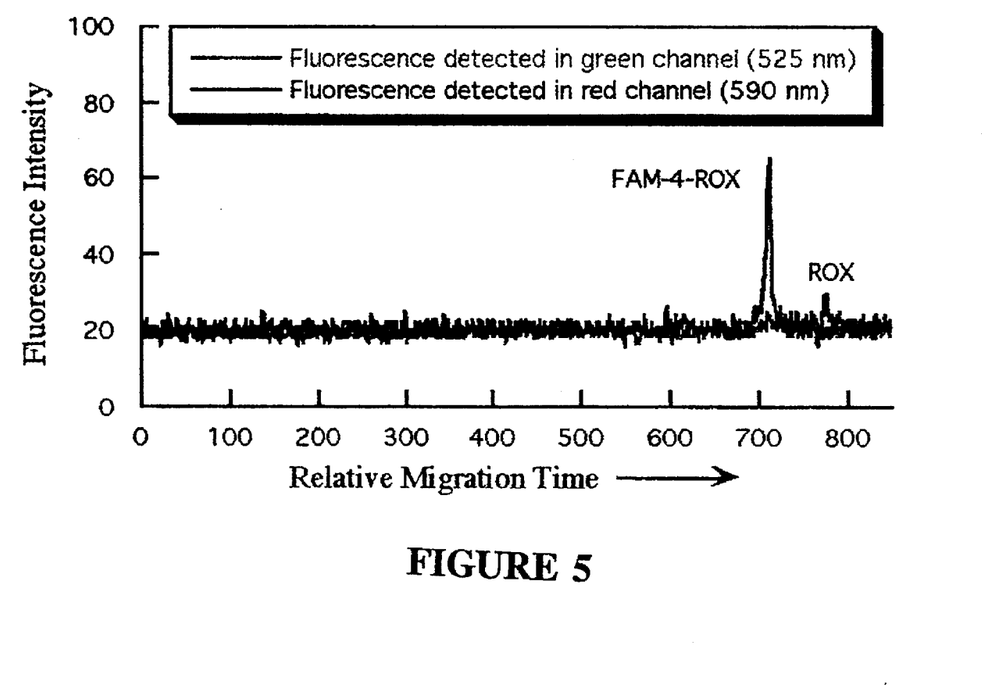
FIG. 5 is a CE electropherogram of FAM-4-ROX and ROX primer. The two primers at the same concentration were mixed together in 80% formamide and injected into the capillary. The fluorescence signals were detected in the green and red channels simultaneously with 476 nm excitation.

The donor dye was attached to the 5' side of the oligomer, and the acceptor dye was attached to the primary amine group on the modified T. The distances between the donor and acceptor were changed by varying the position of the modified T on the oligomer. The primers are denoted as D-N-A, where D is the donor, A is the acceptor and N is the number of bases between D and A. In all the primers prepared, D is Applied Biosystems Inc. ("ABI") dye FAM, a fluorescein derivative, A is ABI dyes TAM or ROX which are both rhodamine derivatives. As a representative example, the structure of FAM-3-TAM is shown below (Structure 2).

running the primer down a capillary electrophoresis (CE) column and detecting in red and green channels. With a FAM- and TAM-labeled primer, nearly all the emission is seen in the red channel (590 nm) (FIG. 2), indicating that the energy from donor FAM was transferred almost completely to the acceptor TAM, producing a Stokes shift of 91 nm. The observation of a single peak indicates the primer is pure. The same outcome is seen for FAM-4-ROX, which gives even a larger Stokes shift of 114 nm (FIGS. 3 and 4). Enhancement of the fluorescence signals of the energy transfer primers compared to single dye labeled primer is seen, where an ABI ROX primer at the same concentration as that of FAM-4-ROX (measured by UV) was injected in the same capillary. The resulting fluorescence signal of FAM-4-ROX is seen to be more than ten times higher than that of the ROX primer (FIG. 5).

Figure 6:
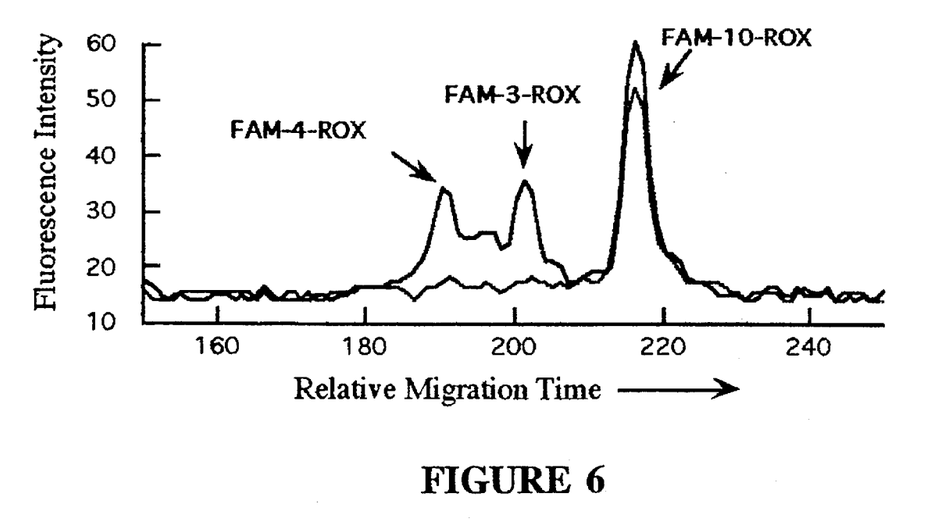
FIG. 6 is a CE electropherogram of a FAM-3-ROX, FAM-4-ROX and FAM-10-ROX mixture, showing the dependence of the mobility on the distance between the donor and acceptor. The sample was analyzed by typical capillary electrophoresis DNA sequencing conditions with 488 nm excitation.

For the successful application of donor-acceptor fluorophore labeled primers to DNA sequencing, it is essential that the primers produce the same mobility shifts of the DNA fragments and display distinct fluorescence signals. It was found that the mobility of the primers depends on the distance between the donor and acceptor (FIG. 6). FAM-4-ROX, FAM-3-ROX and FAM-10-ROX were separated on a capillary and detected in red and green channels. For FAM-10-ROX the increased distance between the dyes reduces the amount of energy transfer, resulting in almost equal signals in the two channels. As the separation distance is reduced, the amount of energy transfer increases as evidenced by the reduced relative green signal. FAM-3-ROX and FAM-4-ROX both exhibit excellent energy transfer, but their mobilities are distinctly different, which offers the potential of tuning the mobility shift by varying the distance. To get an Structure 2.
FAM-3-TAM

Figure 1:
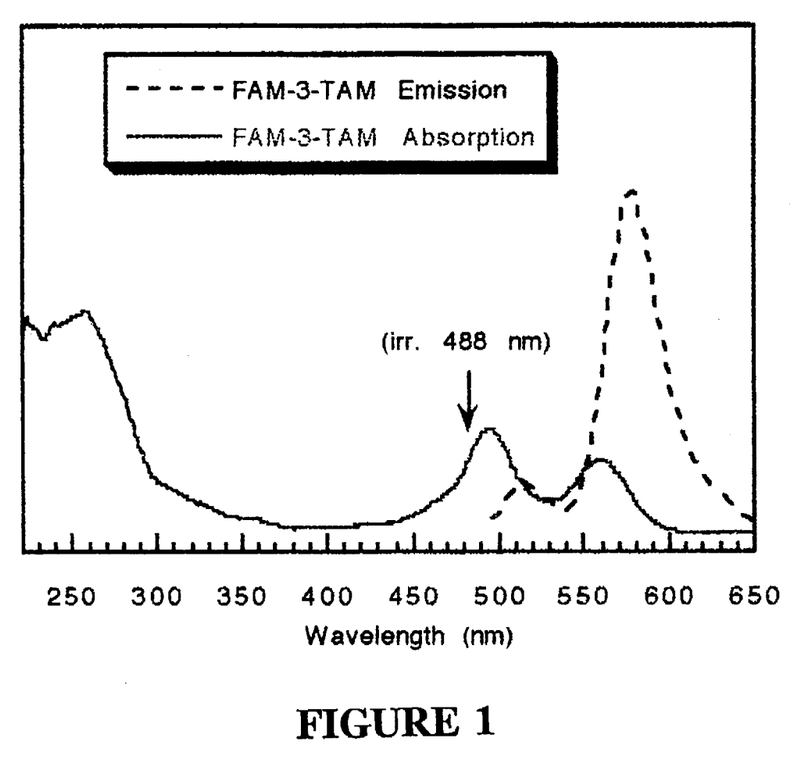
FIG. 1 is a graph of the absorption and emission spectra of FAM-3-TAM in 1xTBE.
Figure 7:
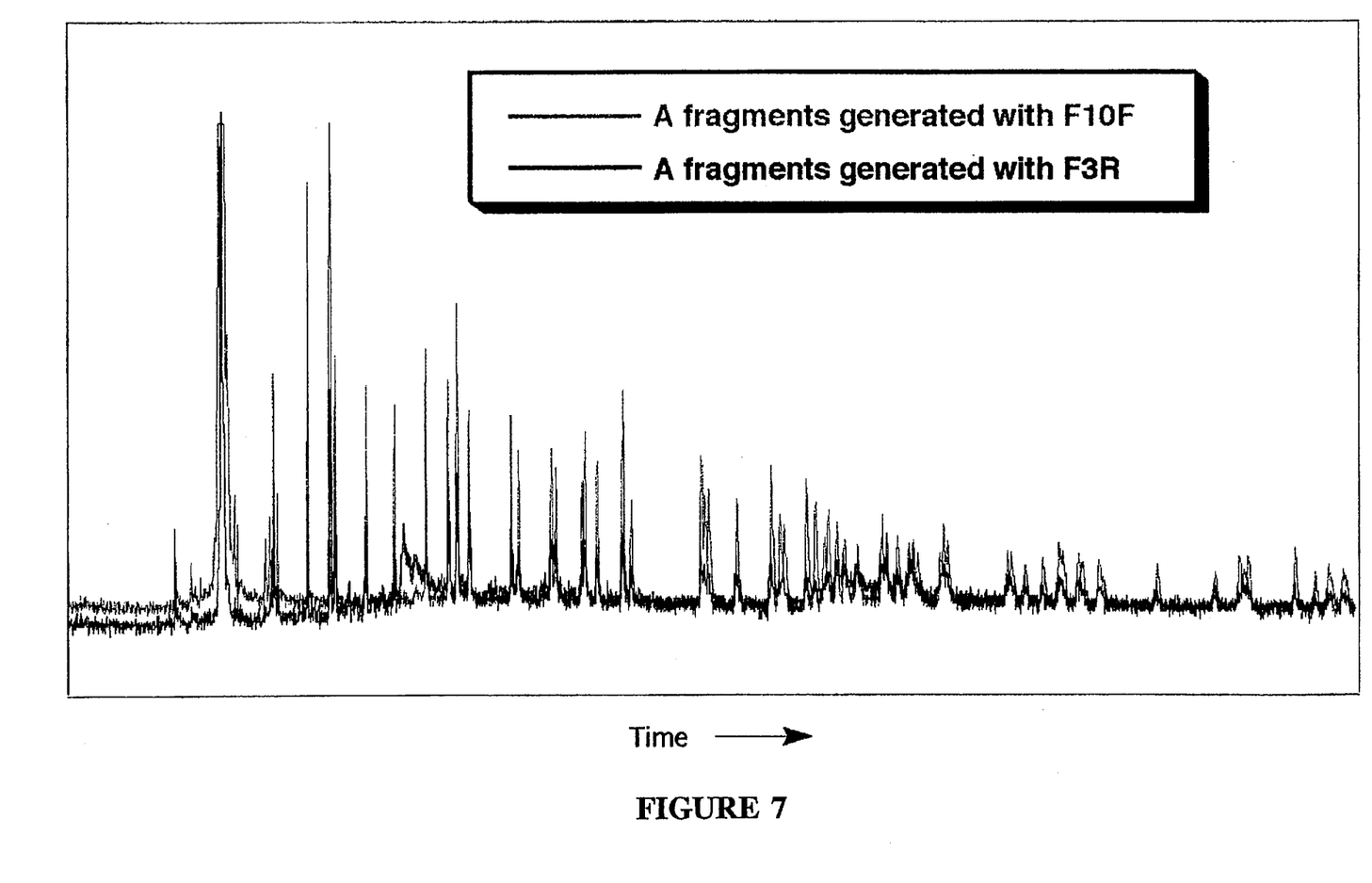
FIG. 7 is a comparison of the mobility shift of different dye primers on M13 mp 18 A fragment DNA samples.

The advantages of the energy transfer approach described here are (1) that a large Stokes shift and much stronger fluorescence signals can be generated when exciting at 488 nm and (2) that the mobility of the primers can be tuned by varying the distances between the donor and acceptor to achieve the same mobility. The visible spectrum of FAM-3-TAM has both the absorption of FAM (495 nm) and TAM (560 nm); however with excitation at 488 nm nearly all of the emission comes out from T with a maximum at 579 nm (FIG. 1). This demonstrates efficient fluorescence energy transfer from FAM to TAM. This can also be seen by exact match of the mobility of two primers that have distinctly different emission spectra, FAM-3-FAM, FAM-4-FAM and FAM-10FAM were also prepared. Among a library of primers prepared (FAM-N-FAM, FAM-N-TAM, FAM-N-ROX), it was found that sequencing fragments terminating in A, generated with FAM-10-FAM and FAM-3-ROX using Sequenase 2, have very similar mobility shifts (FIG. 7), demonstrating the potential for DNA sequence analysis. The emission of FAM-10-FAM and FAM-3-ROX are at 525 nm and 605 nm respectively. The water Raman signals are trivial at these two wavelengths. Thus, the signal to noise ratio is increased dramatically.

I. Preparation of 12-mer Oligonucleotides Containing a Modified T and a FAM Label at the 5' Position.

The following three primers were prepared on an ABI Model 394 DNA synthesizer in a 0.2 μmol scale:

The modified base T* containing an amino linker arm was introduced to the defined position by using Amino-Modifier C6 dT phosphoramidite (Glen Research) and FAM was introduced by using 6-FAM amidite (ABI) in the last step of the synthesis. After the base sequences were completed, the oligonucleotides were cleaved from the solid support (CPG) with 1 ml concentrated $NH_4OH$. The amino protecting groups on the bases (A, G, C and T*) were removed by heating the $NH_4OH$ solution for 4 hours at 55° C. Capillary electrophoresis analysis indicated that the oligomers were ~80% pure, and they were used directly in the next dye-coupling step.

II. Attachment of the Second Fluorescent Dye to the Amino Linker Arm of the Oligomers 1, 2 and 3.

As a representative example, the reaction scheme to couple the second dye (TAM) to the oligomer 1 is shown below:

The FAM-labeled oligonucleotides (1, 2 and 3) in 40 μL 0.5M $Na_2CO_3/NaHCO_3$ buffer were incubated overnight at room temperature with approximately 150 fold excess of either TAM-NHS ester, ROX-NHS ester or FAM-NHS ester in 12 μL DMSO. Unreacted dye was removed by size exclusion chromatography on a Sephadex G-25 column. The two dye labeled oligonucleotides were then purified by 6M urea-TBE, 20% acrylamide gel electrophoresis (40 cm×0.8 cm). The pure primers were recovered from the gel and desalted with Oligonucleotide Purification Cartridge. The purity of the primers was shown to be >99% by capillary gel electrophoresis.

III. Preparation of DNA Sequencing Fragments with FAM-3-ROX and FAM-10-FAM. M13mp18 DNA sequencing fragments terminated in A were produced using Sequenase 2.0 (USB). Two annealing solutions were prepared in 600 μL vials: (1) 10 μL of reaction buffer, 40 μL of M13mp18 single-stranded DNA, and 6 μL of FAM-3-ROX; (2) 6 μL of reaction buffer, 20 μL of M13mp18 single-stranded DNA and 3 μL FAM-10-FAM. Each vial was heated to 65° C. for 5 rain and then allowed to cool to room temperature for 30 min, and then placed on ice for 20 min to ensure that the shorter primers had completely hybridized to the template. 3 μL DTT, 20 μL of ddA termination mixture and 12 μL diluted Sequenase 2.0 were added to each vial on ice. The reaction mixtures were incubated initially at 20° C. for 20 min and then at 37° C. for another 20 min. Reactions were stopped by adding 10 μL 50 mM EDTA, 40 μL 4M $NH_4OH$ and 300 μL 95% EtOH. The solutions were mixed well and then placed on ice for 20 min. The fragments were desalted twice with 75% cold EtOH, dried under vacuum and dissolved in 4 μL of 95% (v/v) formamide and 50 mM EDTA. The sample was heated for 3 min to denature the DNA and then placed on ice until sample injection on the capillary electrophoresis instrument. Electrokinetic injection was performed at 10 kV for 30 s.

It is evident from the above results, that one can tune related compositions, e.g. polynucleotides functionalized with 2 fluorophores to provide for different emission wavelengths and high emission quantum yields, while having substantially the same excitation-light absorbance and mobility. In this way, mixtures of compositions may be independently analyzed, where the different components may be differentially labeled with labels having differing fluorescence emission bands. Furthermore, the compositions can be readily prepared, can be used in a wide variety of contexts, and have good stability and enhanced fluorescent properties.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of separating nucleic acid components of a nucleic acid multicomponent mixture, wherein each of the different nucleic acid components or combinations of components of interest are labeled with different labels comprising different fluorescer pairs, wherein said labels are characterized by: (1) having a donor-acceptor fluorescent pair bonded to an oligonucleotide chain with efficient energy transfer from said donor to said acceptor; (2) each of the donor members of the labels absorbs at substantially the same wavelength as all of the other donor members and each of the acceptor members of the labels emits at a different wavelength compared to any of the other acceptor members; and each of the different labels has substantially the same mobility in said separating as a result of varying the spacer of said donor-acceptor pair along said oligonucleotide chain, with the proviso that one of said labels can have the same fluorescer as the donor and the acceptor;

said method comprising:

binding different labels to different nucleic acid components or combinations of components of said multicomponent mixture;

separating said nucleic acid components into individual fractions; and detecting each of said labeled nucleic acid components by irradiating with a common light source at an absorption wavelength of said donors and detecting the fluorescence of each of said labels.

2. A method according to claim 1, wherein said separation is by electrophoresis.

3. A method according to claim 7, wherein each of said donors of each of said labels absorbs light in the wavelength range of 350–800 nm and each of said acceptors of each of said labels emits light in the wavelength range of 450–1000 nm, wherein when said acceptor is the same as said donor, both absorption and emission are in the wavelength range of 350–800 nm.

4. A method according to claim 3, wherein said acceptor—donor pair are 9-phenylxanthenes.

5. A method according to claim 1, wherein said binding comprises:

combining said labels with said nucleic acid multicomponent mixture, wherein said labels act as primers; and extending said primers under polymerase chain reaction conditions.

6. A kit comprising at least two fluorescent compounds for use as labels, each of said labels characterized by:

(1) comprising an acceptor-donor fluorescent pair bonded to a nucleic acid backbone chain, where the donor efficiently transfers energy to said acceptor for fluorescence of said acceptor; (2) each of the donor members of said labels absorbs at substantially the same wavelength all of the other donor members and each of the acceptor members of said labels emits at a different wavelength compared to any of the other acceptor members; and (3) each of said labels has substantially the same mobility in said separation resulting from varying the spacing of said donor-acceptor pair along said nucleic acid backbone, with the proviso that one of said labels can have the same fluorescer as the donor and the acceptor.

7. A kit according to claim 6, wherein the acceptor and corresponding donor for all of said acceptor-donor fluorescent pairs are separated by not more than about 10 nucleotides.

8. A kit according to claim 6, wherein said donor absorb light in the wavelength range of 350–800 and said acceptors emit light in the wavelength range of 450–1000, wherein when said acceptor is the same as said donor, both absorption and emission are in the wavelength rnage of 350–800 nm.

9. A kit according to claim 8, wherein at least two acceptor—donor fluorescent pairs comprise a xanthene compound.

10. A kit according to claim 9, wherein said xanthene compound is fluorescein or rhodamine.

11. A kit according to claim 6, wherein one of said labels comprises fluorescein and rhodamine.

* * * * *

UNITED STATES PATENT AND TRADEMARK OFFICE
CERTIFICATE OF CORRECTION

PATENT NO. : 5,654,419
DATED : Aug. 5, 1997
INVENTOR(S) : Richard A. Mathies, Alexander Glazer and Jingyue Ju It is certified that error appears in the above-identified patent and that said Letters Patent is hereby corrected as shown below:

At page 1, line 8, insert the heading and paragraph:

--GOVERNMENT RIGHTS NOTICE

This invention was made with Government support under Grant No. DE-FG03-91ER61125, awarded by the U.S. Department of Energy. The Government has certain rights in this invention.--

Signed and Sealed this

Eighth Day of May, 2001

*Attest:*

NICHOLAS P. GODICI

*Attesting Officer*  Acting Director of the United States Patent and Trademark Office